United States Patent
Wozencroft (10) Patent No.: US 8,932,266 B2
(45) Date of Patent: Jan. 13, 2015

(54) AUTOINJECTION DEVICES

(75) Inventor: Robert Michael Wozencroft, Surrey (GB)

(73) Assignee: Owen Mumford Limited, Oxford (GB)

( * ) Notice: Subject to any disclaimer, the term of this patent is extended or adjusted under 35 U.S.C. 154(b) by 742 days.

(21) Appl. No.: 13/058,238

(22) PCT Filed: Aug. 13, 2009

(86) PCT No.: PCT/GB2009/051016
§ 371 (c)(1),
(2), (4) Date: Feb. 9, 2011

(87) PCT Pub. No.: WO2010/018411
PCT Pub. Date: Feb. 18, 2010

(65) Prior Publication Data
US 2011/0144584 A1  Jun. 16, 2011

Related U.S. Application Data (60) Provisional application No. 61/095,477, filed on Sep. 9, 2008.

(30) Foreign Application Priority Data

Aug. 13, 2008 (GB) .................................. 0814747.2

(51) Int. Cl.
*A61M 5/32* (2006.01)
*A61M 5/00* (2006.01)
*A61M 5/20* (2006.01)
*A61M 5/24* (2006.01)
*A61M 5/42* (2006.01)
*A61M 5/46* (2006.01)

(52) U.S. Cl.
CPC ........... *A61M 5/2033* (2013.01); *A61M 5/3257* (2013.01); *A61M 5/24* (2013.01); *A61M 5/326* (2013.01); *A61M 5/425* (2013.01); *A61M 5/46* (2013.01); *A61M 2005/2013* (2013.01); *A61M 2005/206* (2013.01); *A61M 2005/2073* (2013.01); *A61M 2005/2414* (2013.01)
USPC ............ 604/198; 604/187; 604/135; 604/110

(58) Field of Classification Search
CPC ..... A61M 5/2033; A61M 5/24; A61M 5/326; A61M 5/425; A61M 2005/2414; A61M 2005/2013; A61M 2005/206; A61M 2005/2073
USPC ............................................ 604/134–139, 68
See application file for complete search history.

(56) References Cited

U.S. PATENT DOCUMENTS

| 3,880,163 A | 4/1975 | Ritterskamp |
| 5,267,963 A | 12/1993 | Bachynsky |

(Continued)

FOREIGN PATENT DOCUMENTS

| DE | 102005038933 A1 | 2/2007 |
| EP | 0666084 A2 | 8/1995 |

(Continued)

OTHER PUBLICATIONS

International Search Report, dated Dec. 1, 2009, from corresponding PCT application.

(Continued)

*Primary Examiner* — Quynh-Nhu H Vu
*Assistant Examiner* — Jenna Zhang
(74) *Attorney, Agent, or Firm* — Young & Thompson (57) ABSTRACT

An autoinjection device includes a main body 12 in the front end of which is slideably mounted a drawer or front body portion 14. The drawer can be opened to remove or insert a syringe. Closing the drawer while pressing a multifunction button 22 primes the drive mechanism 54, 58 by latching it against trigger latch 66. Pressing the button 22 again while urging the front end causes the drawer to release the trigger latch 66. After the injection the drawer shrouds the used needle and can be released only by pressing the button 22.

7 Claims, 12 Drawing Sheets

(56) References Cited

U.S. PATENT DOCUMENTS

| | | | |
|---|---|---|---|
| 5,271,744 A * | 12/1993 | Kramer et al. | 604/506 |
| 5,273,543 A | 12/1993 | Bell et al. | |
| 5,320,609 A | 6/1994 | Haber et al. | |
| 5,478,316 A * | 12/1995 | Bitdinger et al. | 604/135 |
| 6,099,503 A * | 8/2000 | Stradella | 604/135 |
| 6,123,684 A | 9/2000 | Deboer et al. | |
| 2005/0033234 A1* | 2/2005 | Sadowski et al. | 604/140 |
| 2006/0184189 A1* | 8/2006 | Olson et al. | 606/181 |
| 2006/0264830 A1 | 11/2006 | Hommann | |
| 2009/0259181 A1 | 10/2009 | Moser | |
| 2010/0191184 A1* | 7/2010 | Choi | 604/117 |

FOREIGN PATENT DOCUMENTS

| | | | |
|---|---|---|---|
| GB | 728248 A | 4/1955 | |
| GB | 891887 A | 3/1962 | |
| JP | H06233820 A | 8/1994 | |
| JP | H07222799 A | 8/1995 | |
| JP | H11503637 A | 3/1999 | |
| JP | 2006506185 A | 2/2006 | |
| JP | 2007509657 A | 4/2007 | |
| WO | 03068290 A2 | 8/2003 | |
| WO | 2004098687 A1 | 11/2004 | |
| WO | 2007115424 A1 | 10/2007 | |

OTHER PUBLICATIONS

British Search Report, dated Dec. 15, 2008, from corresponding British application.

Japanese Office Action, dated Sep. 17, 2013, from corresponding JP application.

* cited by examiner

AUTOINJECTION DEVICES

BACKGROUND OF THE INVENTION

This invention relates to autoinjection devices and, in particular but not exclusively, to such devices intended for multiple use.

DESCRIPTION OF THE RELATED ART

Although single use autoinjection devices are common there are many instances where the autoinjection device is designed for reuse by the user or clinician and this is becoming more frequent due to environmental awareness. Where an autoinjection device is to be reused, it is important that the loading, priming, firing and unloading of the syringe is achieved simply and consistently by a wide range of potential users and also that there are safeguards against inadvertent operation.

SUMMARY OF THE INVENTION

According to one aspect of this invention there is provided an autoinjection device comprising:

a housing including a main body portion and a front body portion moveable longitudinally between a closed position and an open position allowing access to enable in use a syringe to be loaded into said housing, the syringe having a body, a plunger and a needle at a forward end of the body;

a drive member and a drive bias means disposed in said housing, the drive member being moveable against said drive bias means to a primed position and operable in use when released from said primed position to urge the syringe forwardly to an injection position, and to expel a dose therefrom; and trigger means for releasably retaining said drive member in its primed position, the device being operable to move said drive member to its primed position as the main body and the front housing portion are moved to their closed position.

In this way preferred arrangements of the device may be opened to insert a syringe and then closed to prime the drive mechanism.

To provide a safety feature, at least one of said front housing portion and said drive member is preferably moveable between an inactive configuration, in which closing movement of the front housing portion does not cause engagement with said drive member, and an active configuration, in which closing movement of said front housing portion applies directly or indirectly a rearward force to said drive member to move it to said primed position.

Thus the front housing portion may include a drive face adapted to be moved to cooperate with a drive face on the drive member.

An externally operable actuating member may be disposed on the main body portion and actuable to urge the drive faces into lateral engagement against a bias.

Conveniently, said front housing portion is operable to apply directly or indirectly a force to release said trigger means on movement of the front housing portion rearwardly from said closed position.

Again, for safety, at least one of said front housing portion and said trigger means may be changeable between an inactive configuration in which rearward movement of said front housing to engage said trigger means is prevented, and an active configuration, wherein, on rearward movement from said closed position, said front housing portion releases said trigger means.

An externally operable actuating member may be disposed on the main body portion and operable to switch the front housing portion and the trigger means to their active configuration.

A dual function actuating member may be provided for activating the priming stroke and for freeing the front housing portion for rearward motion to release the trigger means.

This safety feature may be provided by providing releasable safety latch means for preventing rearward movement of said front housing portion to release said trigger means until after said safety latch has been released.

Still further, to ensure that the needle is shrouded after an injection a lock out latch means may be provided for latching the forward housing portion against retracting means when it returns to a forward position on completion of an injection.

Both latching functions may be performed by a common releasable latching means. Indeed, in a particularly preferred arrangement a common actuating member and latching means may be provided.

To facilitate the injection, the housing may have an associated injection site contacting element having two lobes spaced to either side of the longitudinal axis of the needle and adapted in use, when the contact element is pressed against the user's flesh, to compress the flesh at spaced locations to either side of the injection axis and thereby to cause a bulge at the injection site.

Preferably said injection site contact element has only two lobes, and the contact element has a profile comprising a central concave region with two convex regions to either side thereof to define said lobes. In one arrangement said lobes are adapted to move towards each other as pressure is applied to said device, thereby to exert a pinching action to enhance said bulging effect.

In another aspect, this invention provides an autoinjection device comprising:

a housing having a main body portion, containing a drive mechanism, and a front body portion moveable longitudinally between a closed position and an open position allowing access to enable a syringe to be loaded therein for an autoinjection cycle, wherein closing of said housing is operable to energise the drive mechanism for the autoinjection cycle, and rearward movement of said front body portion beyond the closed position releases said drive mechanism.

The device advantageously includes an externally operable actuating member, operarable to affect at least one of the following functions:

to engage and/or disengage a load path between the forward body portion and a prime mover in the drive mechanism, to engage and/or disengage a load path between the forward body portion and a trigger for the drive mechanism, to prevent and/or allow rearward movement of the forward body portion prior to release of said trigger, to prevent and/or allow rearward movement of the forward drive portion from a shrouding position after completion of said injection operation.

In yet a further aspect, this invention provides an injection device comprising:

a housing including a main body portion and a front body portion relatively moveable longitudinally;

the housing being openable to provide access to allow a syringe to be loaded into the housing in use, the syringe having a body, a plunger and a needle at its forward end;

a drive member disposed within the housing and moveable against a drive spring bias to a primed position and operable in use when released from said primed position to urge the syringe forwardly within the housing to an injection position in which the syringe needle projects from the front end of the housing and to expel a dose therefrom;

a trigger for latching said drive member in its primed position;

said front body portion further being moveable against a housing spring bias rearwardly from a closed position to a fire position in which it unlatches said firing latch to free said drive member for forward movement under the influence of said drive spring bias;

wherein as said housing is moved away from the injection site following an injection, said housing spring bias urges said front body portion forwardly back towards its closed position to shroud said needle;

a releasable safety latch preventing rearward movement of said front body portion from its closed position until release of the safety latch, and a latch for latching said forward body portion in its extended, shrouding, position.

Preferably said front body portion is movable longitudinally relative to said main body portion from said closed position to an open position providing access for said syringe. The front housing portion may include a drive face adapted to be moved to cooperate with the drive member to move the drive member to its primed position as the housing is moved from its open position to its closed position. An actuating member may be disposed on the main body portion for urging the drive face on the front body portion laterally into engagement with the drive member.

The said actuating member may also be operable to unlatch said safety latch whereby, at different phases of operation of the device, said actuating member is operable to urge said drive face on the forward drive portion into engagement with the drive member to release said forward body portion to allow it to move from said closed position to its firing position, and to lock out the forward drive portion on completion of an injection.

Preferably said front body portion includes a unitary element slideably mounted for telescopic movement relating to said main body portion. Said unitary front body portion may include a shroud region for said needle, a latch surface for cooperating with said releasable safety latch, and a drive face resiliently moveable into engagement with said drive member. The drive member is preferably longitudinally slideably mounted within said housing, with said drive spring bias comprising at least one spring. The drive spring bias preferably comprises two co-acting springs, which advantageously each comprise a constant force spring.

Conveniently, said housing includes at its forward end thereof an interchangeable nose element, the contact nose element being interchangeable to adjust the penetration depth of the injection.

In another aspect, this invention provides an injection device comprising:

a housing;

said housing being adapted in use to receive a syringe having needle at its forward end;

a drive member moveable against a spring bias to a primed position and releasable in use to urge said syringe to a forward position and to expel a dose;

a trigger for latching said drive member in its primed position;

an actuating member having a shroud portion at a forward region thereof and moveable between a forward position and a rearward position;

actuating member bias means biasing said actuating member towards its forward position;

said actuating member being adapted in use when moved to its rearward position to release said firing latch to free said drive member for movement;

the actuating member thereafter being movable forward under the influence of said actuating member bias means to return to its forward position with said shrouding region in use shrouding the needle when the needle is at its forward position, and releasable latch means for locking said shroud member against movement from its forward position.

In yet another aspect this invention provides an injection device comprising a needle through which a dose is delivered and, adjacent said needle, a skin contact surface, said skin contacting surface comprising two lobes spaced to either side of the longitudinal axis of the needle and, adapted in use, when the contact element is pressed against the skin, to compress the flesh space locations to cause a bulge at the injection site.

In still a further aspect, this invention provides an autoinjection device comprising a housing for receiving a syringe, and having a drive mechanism for releasable to urge the syringe forwardly to an injection position and to expel a dose therefrom, said drive mechanism comprising a drive member mounted for sliding movement within said housing and acted upon by two constant force spring arrangements.

Whilst the invention has been described above, it extends to any inventive combination or sub-combination of the features set out above, or in the following description or claims.

BRIEF DESCRIPTION OF THE DRAWING FIGURES

The invention may be performed in various ways, and embodiment thereof will now be described by way of example only, reference being made to the accompanying drawings in which:

FIGS. 5(*a*) and (*b*) are a view of the injection device when closed in a primed condition with the top cover removed, and a detail showing the latch mechanism respectively;

FIGS. 10(*a*) and (*b*) are schematic section views of a modified form of nose designed actively to exert a pinching action on the injection site.

DETAILED DESCRIPTION OF THE INVENTION

Referring initially to FIGS. 1 to 4 the reusable auto injector of the present invention is designed to have a slim compact rectangular form closed of length not much greater than that of the syringe and needle cap.

Figure 3:
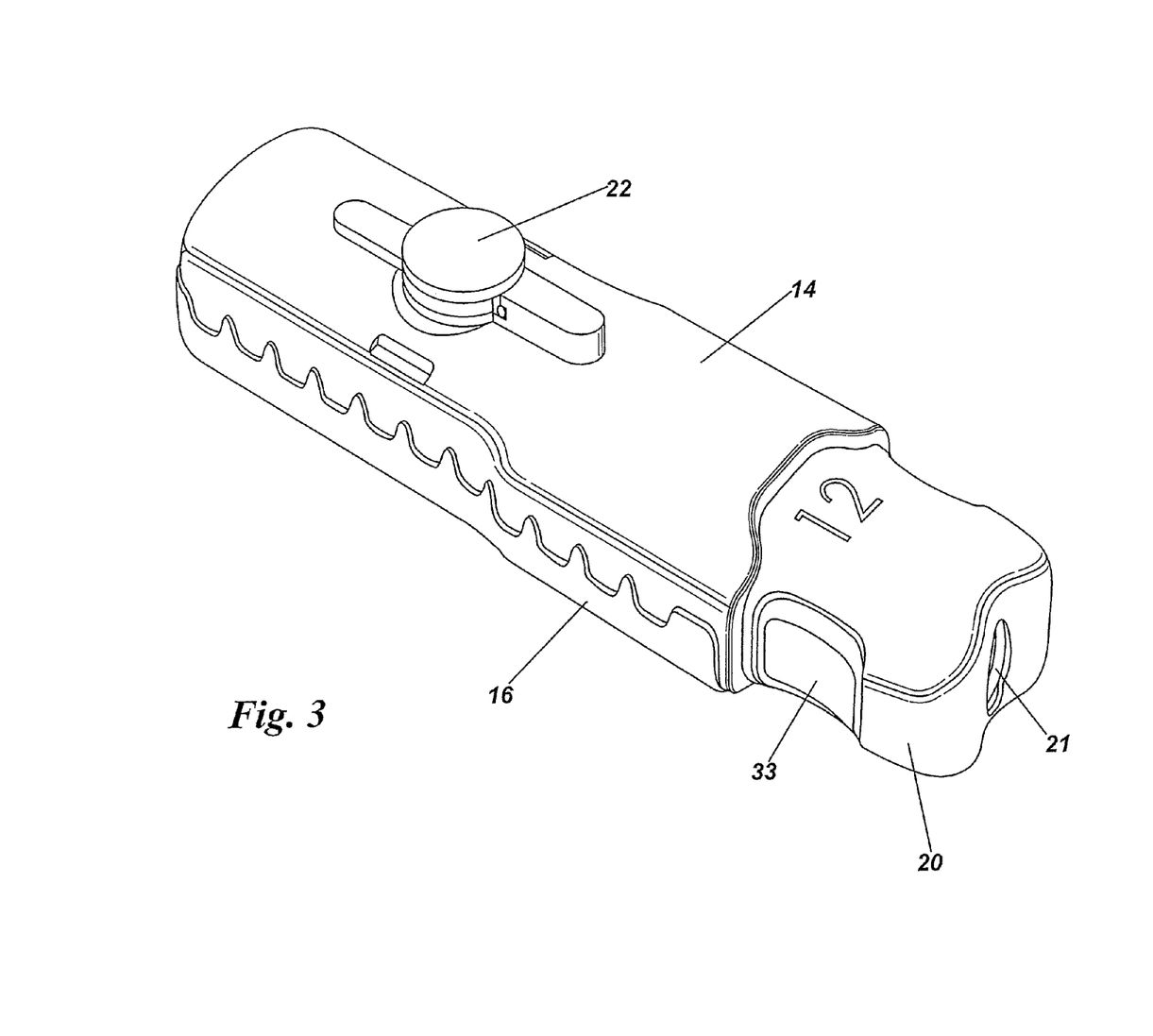
FIG. 3 is a bottom perspective view when closed.

The auto injector indicated generally at 10 comprises a main body portion 12 made up of a lower casing part 14 and an upper casing part 16 to define a body of generally rectangular form open at one end to receive slideably a drawer or front body portion 18. On the forward end of the drawer 18 is a nose piece 20. The nose piece may be interchangeable so as to provide a number of options for the injection depth. Typically injection depth may be 8, 10 and 12 mm penetration depth. On the underside of the housing, as seen in FIGS. 3 and 4, there is a multi-function button 22 having an integral forwardly extending arm 24 and being mounted for rocking movement in the lower casing part 14.

Figure 4:
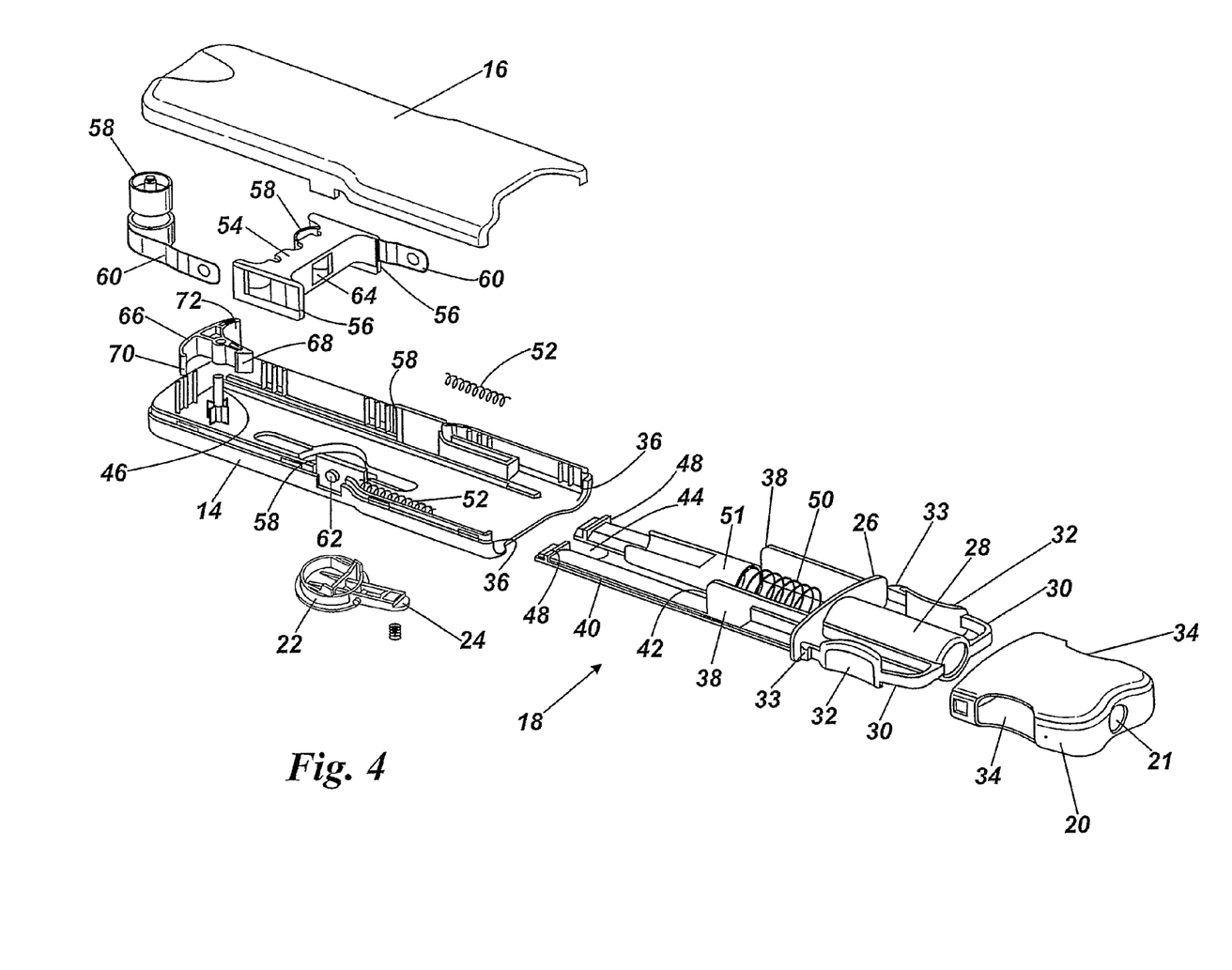
FIG. 4 is an exploded view of the injection device.
Figures 5A, 5B:
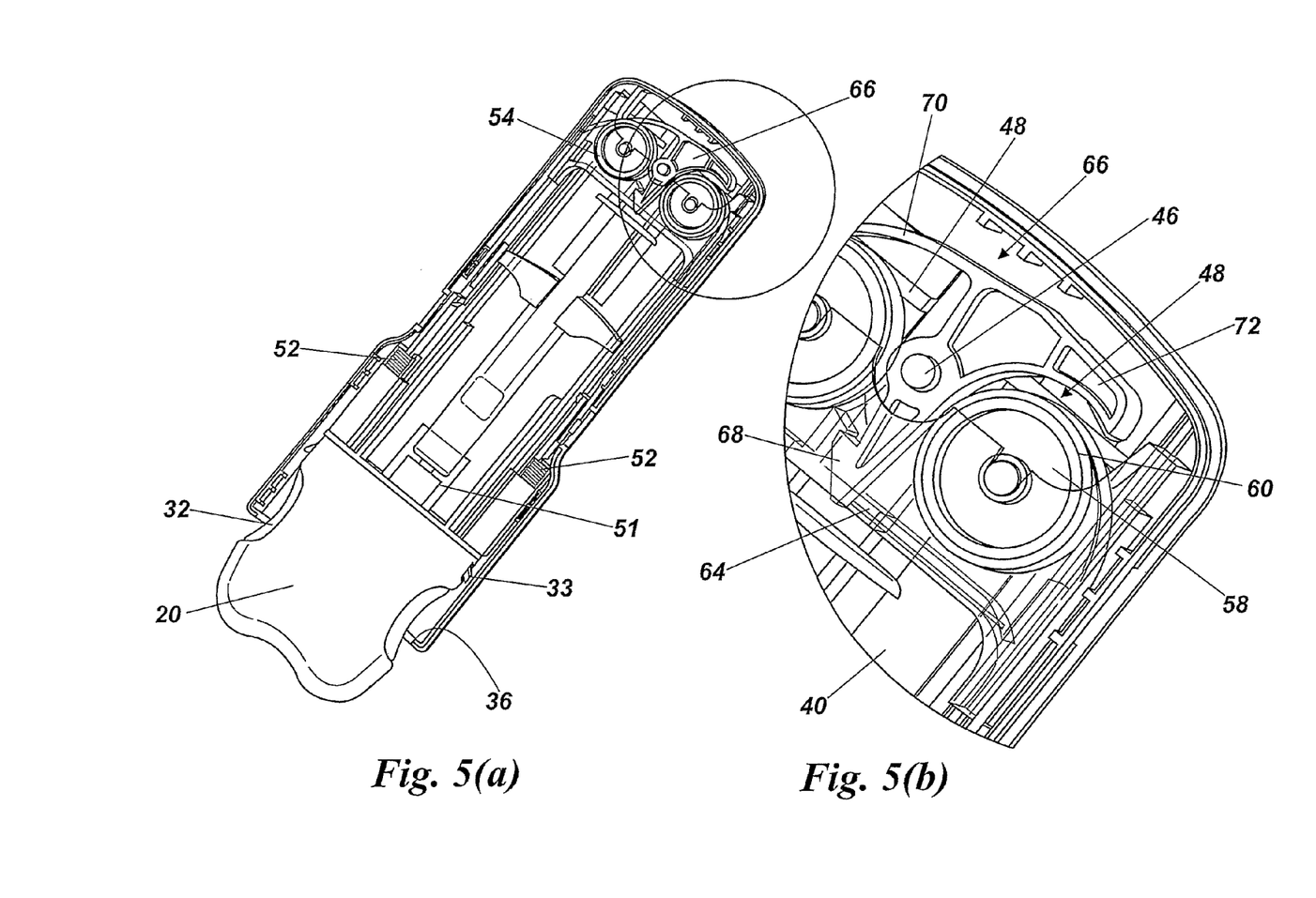
Figure 6:
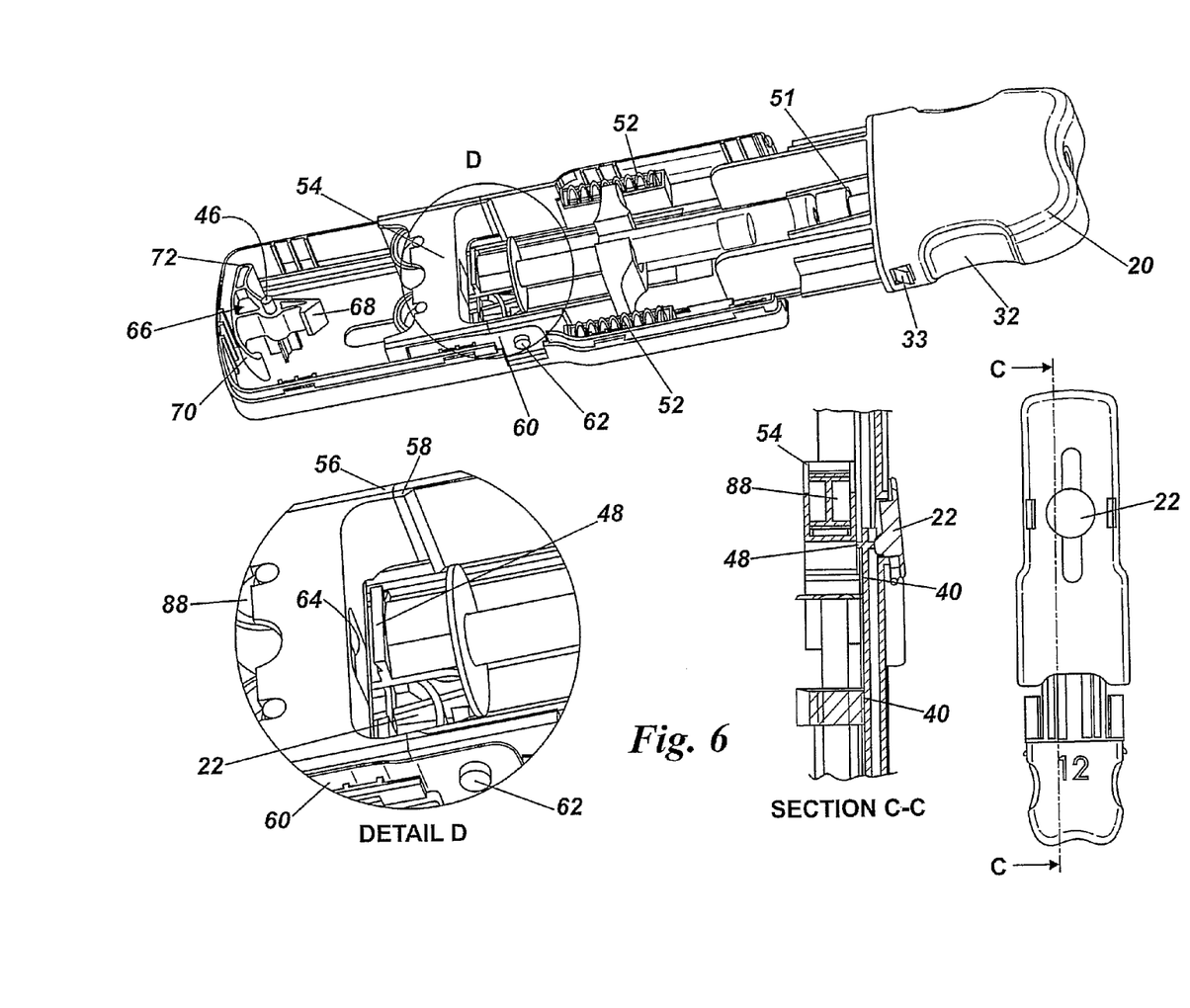
FIG. 6 are respective views of the injection device at the start of a priming action with the multi-function button depressed and urging the rear part of the drawer into engagement with the drive member, a detail on said view, and a detailed section view respectively.
Figure 7:
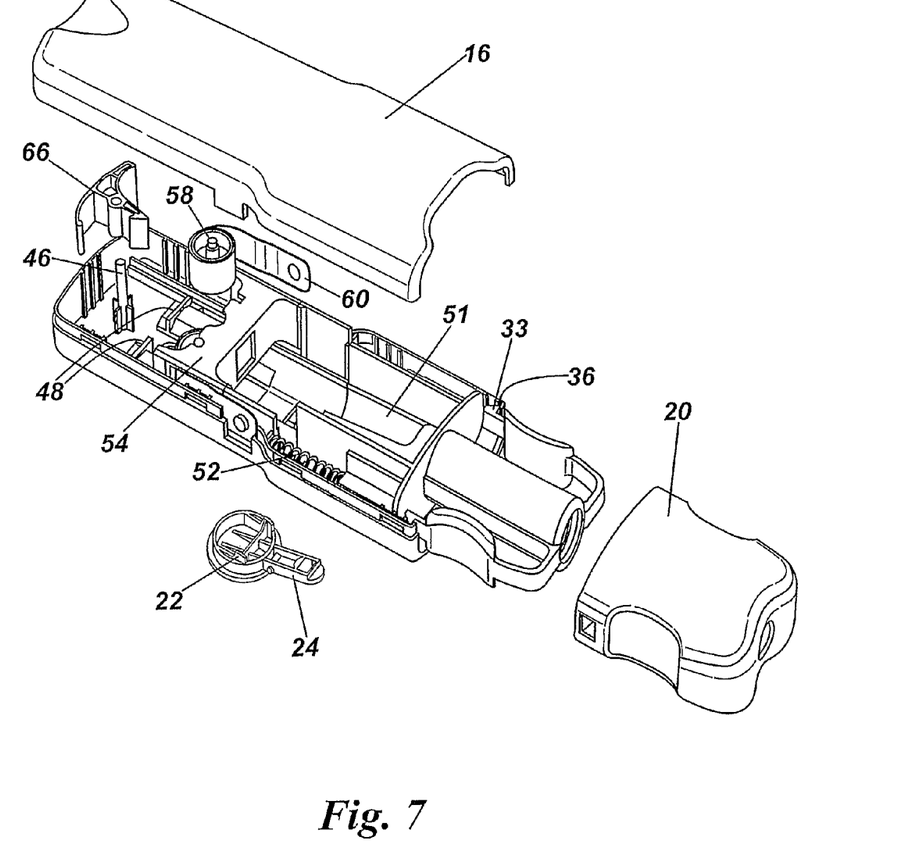
FIG. 7 is a part-assembled view of the injection device.
Figure 8:
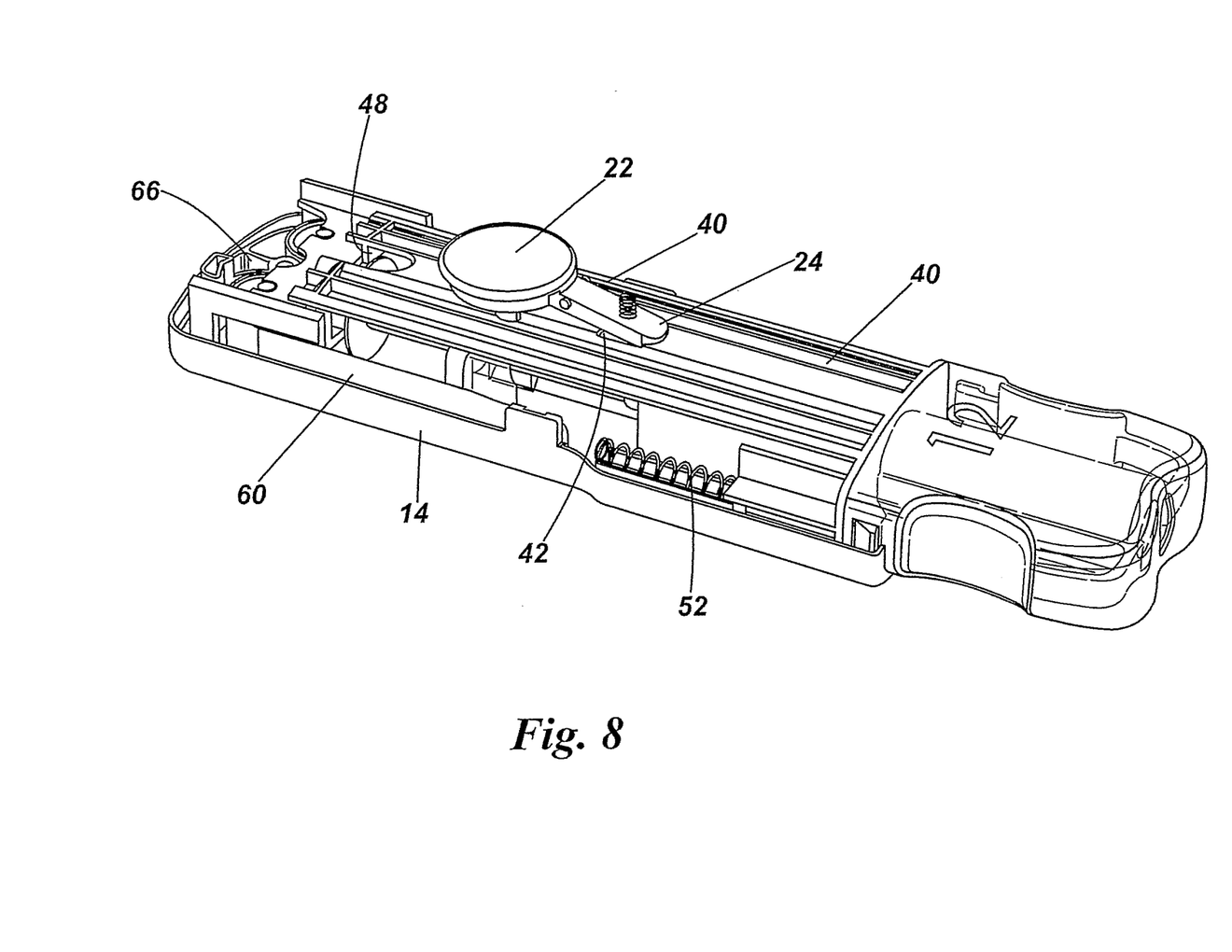
FIG. 8 is a view from the underside of the injection device with the lower body removed showing interaction of the button and the drawer.

Turning more specifically to FIG. 4, the drawer 18 comprises a main transverse web 26 from which extends forwardly a cylindrical tubular portion 28. From the front end of the tubular portion 28 extends first laterally then rearwardly two spring arms 30 with finger pads 32 that align with apertures 34 in the nose piece 20. At their rearward ends, the spring arms 30 terminate in barbed portions 33 which latch behind abutment surfaces inside an inner lip 36 of the main body portion 12 releasably to latch the drawer in its closed position. Extending rearwardly from the main web 26 are two side webs 38 between which there is a floor 40 extending well to the rear of the webs 38. The drawer in this embodiment is formed integrally from a single plastic moulding. In the floor, just to the rear of the side webs 38 is a latch aperture 42 that cooperates with the arm 24 of the multi-function button 22 in a manner to be described below.

At the rear end the floor 40 has a cut out to accommodate a pivot post 46 upstanding from the lower casing 14. Upstanding from the spaced edges of the floor 40 to either side of the cut out portion 44 are upwardly projecting ribs 48. Slideably received in the inside of the tubular portion 28 of the drawer 18 is a compression spring 50 and the forward end of a part cylindrical syringe carriage 51 cut away to allow a syringe to be introduced as to be described below. The drawer 18 is urged forwardly by twin drawer springs 52 which are received inside pockets on the lower body casing and act against the main web 26 of the drawer to push it forwardly so that the barbs 33 are normally in engagement with the lip 36 on the housing.

Slideably mounted in the lower casing part 14 is a drive member 54, the forward extent of movement of the drive member 54 being limited by horns 56 on the drive member abutting internal ribs 58 on the lower casing 14. The drive member is urged forwardly relative to the lower casing by a pair of constant spring arrangements each comprising a drum 58 rotatably mounted on the drive member around which is wrapped a constant force spring 60 whose apertured free end is anchored to the lower casing 14 by a peg 62. By using twin constant force spring arrangements the loading on the drive member is symmetric and also the size of the springs required can be reduced thereby giving a flatter, more compact arrangement. The lower casing 14 may be provided with 'end of dose' apertures through which part of the drive member 54 is visible only when it is in its fully forward position with the horns 56 adjacent the abutments 58. The drive member 54 has a latching aperture 64 which cooperates with a T-shaped latch 66 which is mounted for pivoting movement on the pivot post 48. At the base of the T of the latch 66 is a barbed latch surface which engages the latch aperture 64 releasably to retain the drive member in a primed position against the bias afforded by the constant force springs 60. One of the cross limbs of the latch 66 is anchored in the lower casing 14 and acts as a resilient bias 70 urging the barb 68 to its latching position. The other cross piece of the latch comprises an abutment surface 72 that is engageable by one of the ribs 48 on the rear end of the drawer when suitably deflected upwards by the multi-function button 22.

Figure 1:
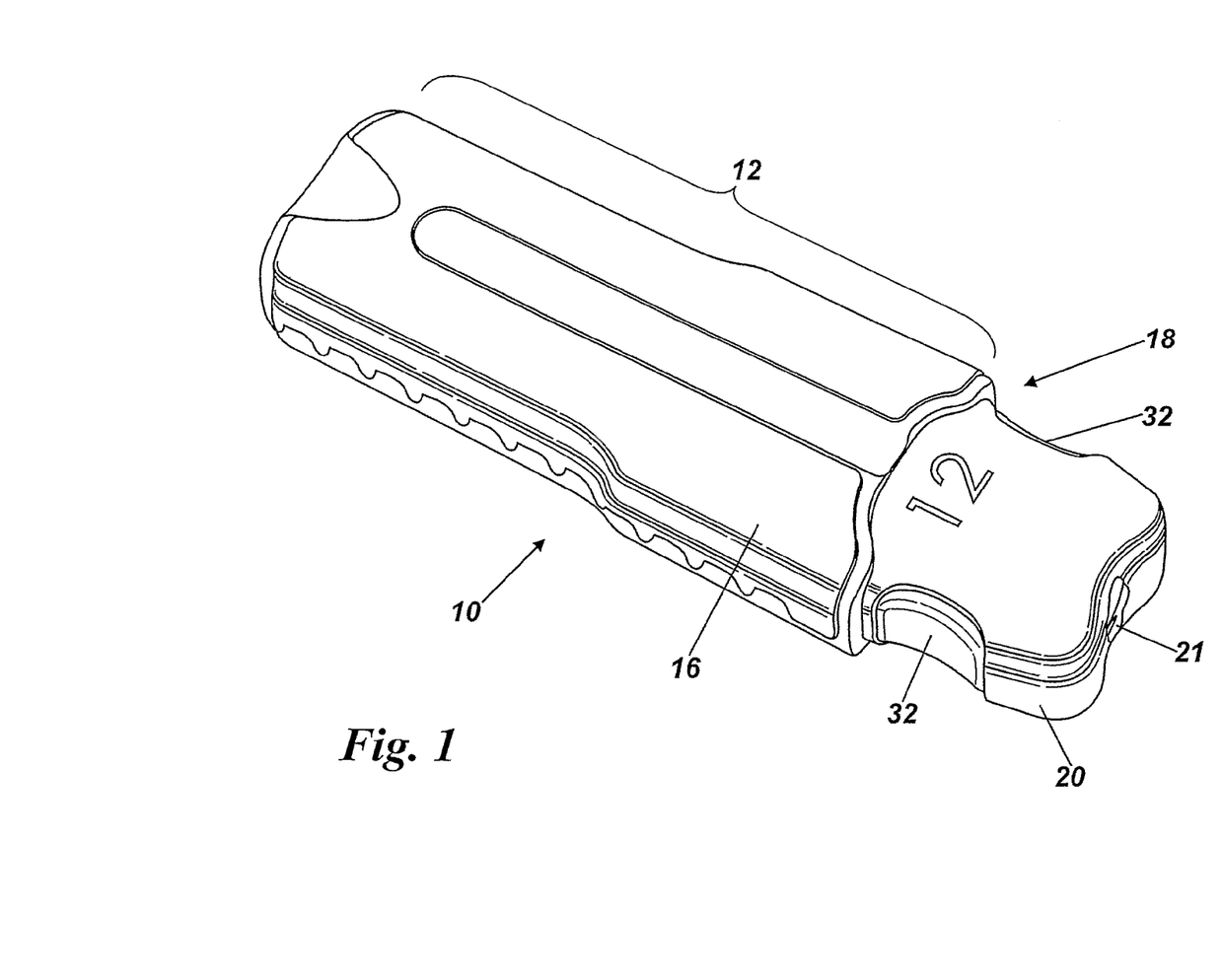
FIG. 1 is a top perspective view of the injection device when closed.
Figure 2:
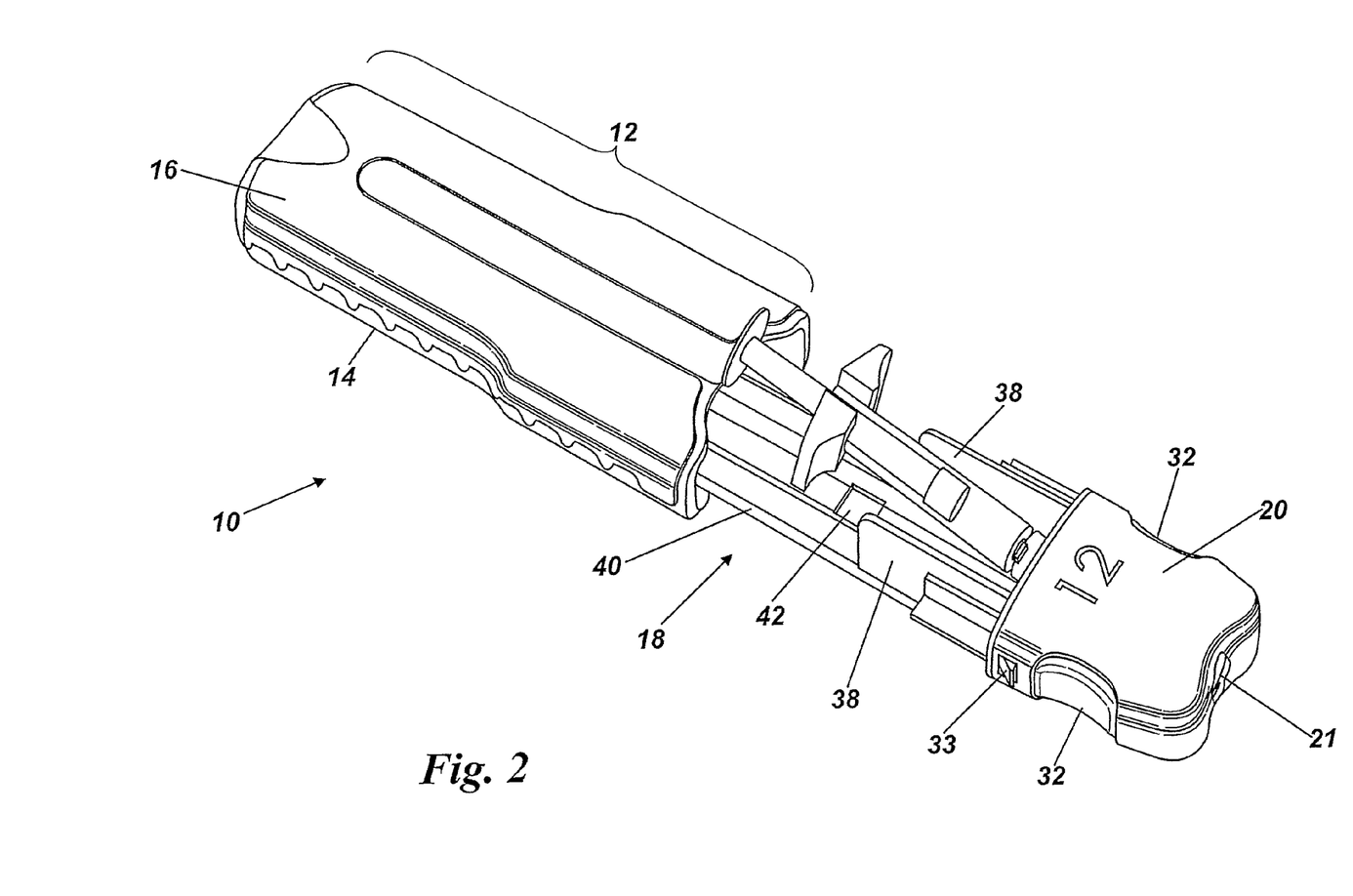
FIG. 2 is a top perspective view of the injection device when open for insertion of a syringe.

Referring now to FIGS. 11(a) to (f) operation of the device will now be described. From a closed position as shown in FIGS. 1 and 3, the device is moved to an open position by squeezing the finger pads 32 thus pulling the barbs 33 out of engagement with the lip 36 and pulling the drawer forwardly to allow access to the syringe carriage 51 (FIG. 11(a)). A syringe may then be inserted into the carriage 51 and dropped into place (FIG. 11(b)). In doing this the needle cap is trapped by the keyhole shaped opening 21 in the nose piece 20, thus holding the syringe forwardly in the drawer against the bias of the carriage spring 50 (FIG. 11(c)). When the needle cap is removed, the syringe springs back to become captive inside the device thereby shrouding the needle.

Figure 11A:
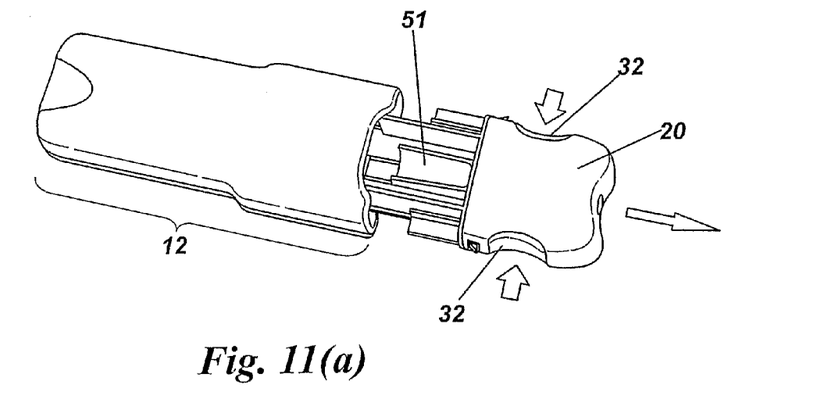
FIGS. 11(a) to (f) illustrate successive stages during operation of the device of FIGS. 1 to 8.
Figure 11B:
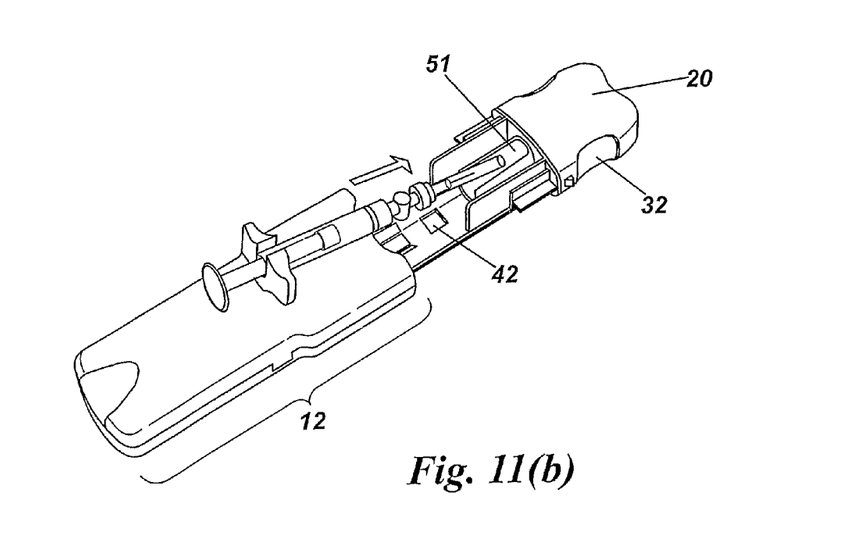
Figure 11C:
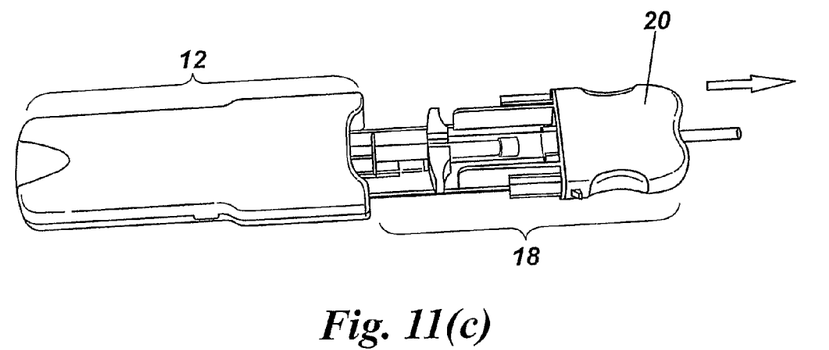
Figure 11D:
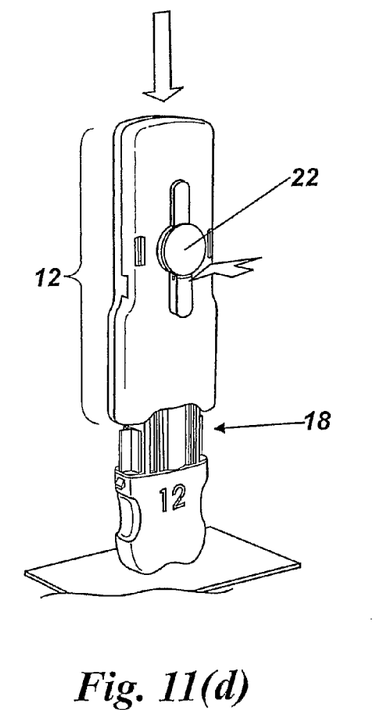

In order to prime the device, the multi-function button 22 is pressed which in turn presses the floor 40 of the drawer away from the opposed surface of the lower casing 14 so that the ribs 48 are aligned with a transverse surface of the drive member 54. At the same time the device is pushed down on a flat surface (FIG. 11(d)) to push the drawer 18 back into the main body and at the same time pushing the drive member 54 rearwardly until it is latched in the primed position by means of the latch 66. As the drawer returns to its closed position, the barbs 33 move past the inward lip 36 and prevent forward movement of the drawer. At the same time the arm 24 on the multi-function button 22 latches in latch aperture 42 in the floor 40 of the drawer 18, to prevent rearward movement. It will be noted that the device cannot be primed without the compound action of both pressing the multi-function button 22 and pushing the nose against a firm surface to move the drive member 54 rearwardly to latch it.

Figure 11E:
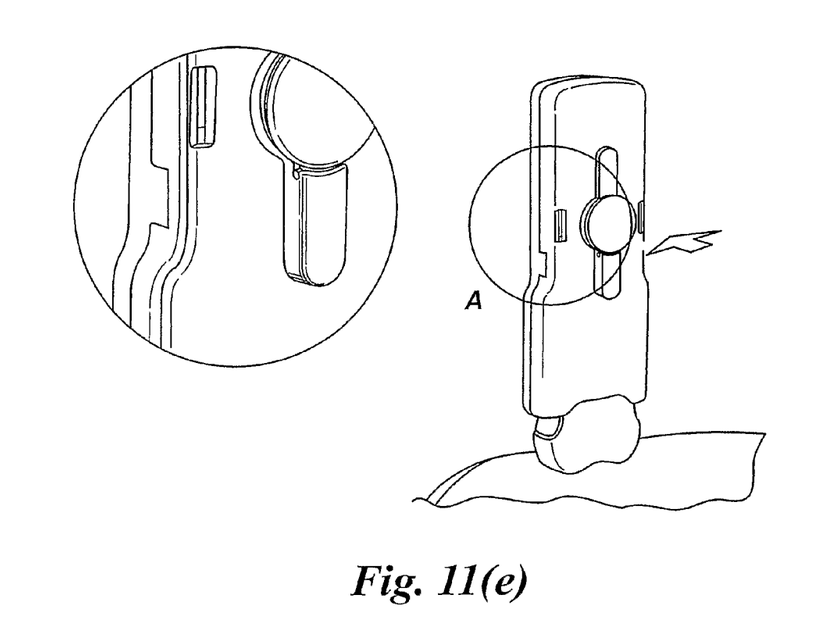
Figure 11F:
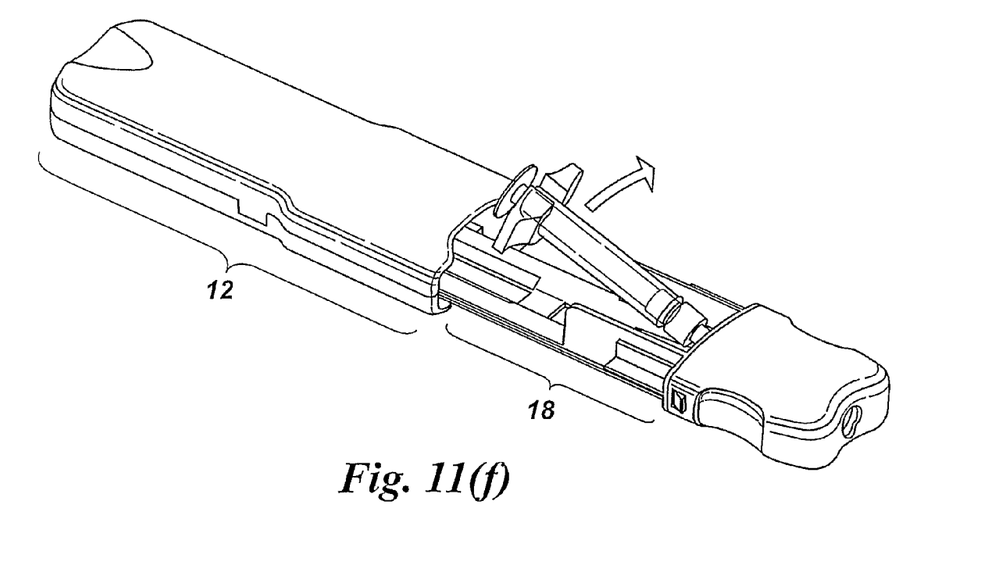

In order to fire the device it is offered up to the injection site (FIG. 11(e)) and the multi-function button 22 depressed to exert two functions; firstly, it lifts the arm 24 out of the latching recess 42 so allowing the drawer to move back into the housing towards the firing position and secondly, it again lifts the floor 40 of the drawer away from the internal surface of the lower casing so that the right hand rear rib 48 as viewed in FIG. 4 is aligned with the abutment surface on the trigger and so as the drawer reaches its rearmost position, it pivots the latch 66 thus releasing the drive member 54. The drive member moves under the influence of the constant force springs firstly to drive the syringe forwardly and thereafter to expel a dose as the plunger moves relative to the syringe. It is to be noted that, unless the button 22 is pressed to lift the floor of the drawer 40 upwardly, the rib 48 will simply pass underneath the abutment 72 and thus not trip the latch. This embodiment therefore requires that, for an injection to occur, there must be sustained pressure applied to the multi-function button 22 not only to release the drawer for rearward movement but also to ensure that the rib 48 engages the release abutment.

When the user releases pressure from the main body portion on completion of an injection, the drawer 18 moves back forwardly to its initial position under the influence of the drawer springs 52 and in so doing, shrouds the needle of the syringe. As it nears the rest position, the finger 24 again latches into the latch aperture 42 on the drawer thus effectively locking the drawer against retraction movement and ensuring that the needle remains shrouded.

Finally, to unload the device, the finger pads 32 are pressed and the drawer moved forwardly to allow access to the syringe which is removed.

Figure 9:
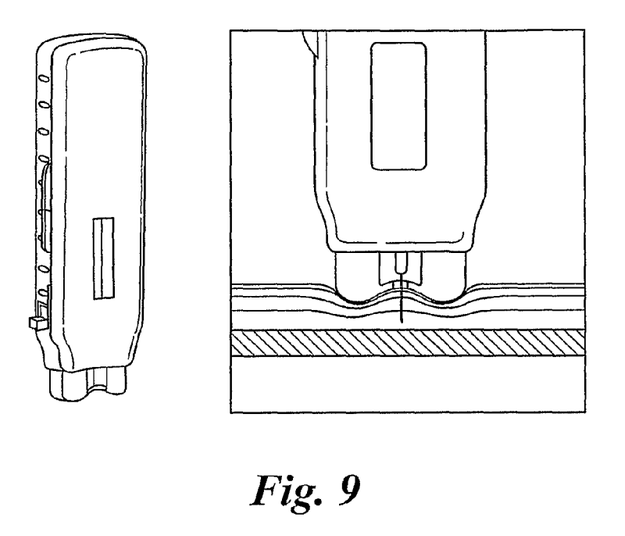
FIG. 9 is a schematic view showing the effect of the wide footprint of the nose of the injection device when applied to a user's skin.
Figure 10A:
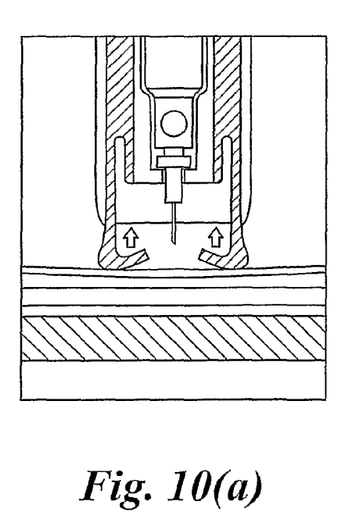
Figure 10B:
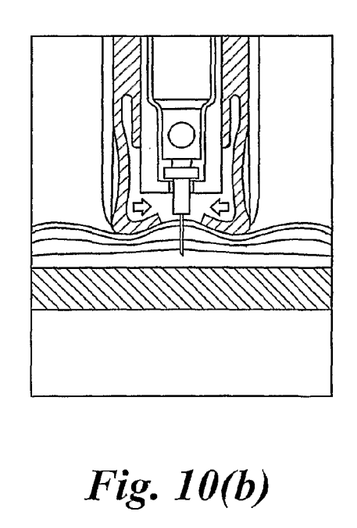

Referring to FIGS. 9 and 10, the traditional method of administering a subcutaneous injection with a syringe (without an auto injector) is to pinch the flesh skin at the injection site and to insert the needle at the centre of the pinched fold of skin. This creates depth in the subcutaneous layer ensuring the needle does not enter the muscle layer below, it also relieves pressure under the skin thereby making it easier to inject the drug. With some known types of auto injector, the surface area of the device contacting the skin is typically relatively small and immediately adjacent the injection axis. Such devices can therefore have the effect of actually thinning the subcutaneous layer due to the pressure and increasing pressure under the skin, especially if the footprint is small. However in the present embodiments it will be noted that the nose 20 has a rounded 'w' profile where it contacts the injection site, defining two lobes 72 to either side of the injection axis. Applying pressure to two spaced locations to either side of the injection axis provides an effect similar to the pinching action commonly used when injecting into the subcutaneous layer.

It will be appreciated that this contact surface may be used on a wide variety of different devices beyond the embodiments described herein.

FIGS. 10 (*a*) and (*b*) describe a variation of this technique where the lobes of the injection contact surface instead of being static are defined on the ends of flexible arms which are configured such that as pressure is applied to the arms, the contact surfaces tend to move together thus enhancing the pinch effect. Thus in these Figures, the forward end of the housing is provided with two inwardly facing L-shaped members with rounded contact surfaces designed to roll inwards as pressure is applied.

The invention claimed is:

1. An injection device comprising:
    a housing including a main body portion and a front body portion relatively moveable longitudinally;
    the housing being openable to provide access to allow a syringe to be loaded into the housing in use, the syringe having a body, a plunger and a needle at a forward end of the body;
    a drive member disposed within the housing and moveable against a drive spring bias to a primed position and operable in use when released from said primed position, said drive bias being sufficient to urge the syringe forwardly within the housing to an injection position in which the syringe needle projects from the front end of the housing and thereafter to expel a dose therefrom;
    a trigger for latching said drive member in said primed position;
    said front body portion further being moveable against a housing spring bias rearwardly from a closed position to a fire position that unlatches said trigger to free said drive member for forward movement under the influence of said drive spring bias;
    wherein as said housing is moved away from the injection site following an injection, said housing spring bias urges said front body portion forwardly back towards said closed position to shroud said needle;
    a releasable safety latch preventing rearward movement of said front body portion from said closed position until release of the safety latch, and
    a latch for latching said forward body portion in a extended, shrouding position.

2. An injection device according to claim 1, wherein said front body portion is movable longitudinally relative to said main body portion from said closed position to an open position providing access for said syringe.

3. An injection device according to claim 1, wherein the front housing portion includes a drive face adapted to be moved to cooperate with the drive member to move the drive member to said primed position as the housing is moved from an open position to said closed position.

4. An injection device according to claim 3, including an activating member is disposed on the main body portion for urging the drive face on the front body portion laterally into engagement with the drive member.

5. An injection device as claimed in claim 4, wherein said actuating member also is operable to unlatch said safety latch whereby, at different phases of operation of the device, said actuating member is operable
    to urge said drive face on the forward drive portion into engagement with the drive member,
    to release said forward body portion to allow said forward body to move from said closed position to a firing position, and
    to lock out the forward drive portion on completion of an injection.

6. An injection device according to claim 1, wherein said front body portion includes a unitary element slideably mounted for telescopic movement relating to said main body portion.

7. An injection device according to claim 6, wherein said unitary front body portion includes a shroud region for said needle, a latch surface for cooperating with said releasable safety latch, and a drive face resiliently moveable into engagement with said drive member.

* * * * *